US012606476B2

(12) United States Patent
Oh et al.

(10) Patent No.: US 12,606,476 B2
(45) Date of Patent: Apr. 21, 2026

(54) BIOGAS PRODUCTION SYSTEM USING ORGANIC WASTE

(71) Applicants: KMJ International Inc., Redbank, NJ (US); DHM Global Inc., Annandale, VA (US)

(72) Inventors: Insub Oh, Incheon (KR); Sinsook Cho, Incheon (KR); Myungkeun Oh, Matawan, NJ (US); Bongyul Tak, Bucheon-si (KR); Bongsik Tak, Seoul (KR)

(73) Assignees: KMJ International Inc., Redbank, NJ (US); DHM Global Inc., Annadale, VA (US)

( * ) Notice: Subject to any disclaimer, the term of this patent is extended or adjusted under 35 U.S.C. 154(b) by 392 days.

(21) Appl. No.: 18/306,441

(22) Filed: Apr. 25, 2023

(65) Prior Publication Data

US 2024/0360021 A1     Oct. 31, 2024

(51) Int. Cl.
| | |
|---|---|
| *C02F 11/04* | (2006.01) |
| *C07C 9/04* | (2006.01) |
| *C02F 103/20* | (2006.01) |

(52) U.S. Cl.
CPC ............... *C02F 11/04* (2013.01); *C07C 9/04* (2013.01); *C02F 2103/20* (2013.01); *C02F 2303/10* (2013.01); *Y02E 50/30* (2013.01); *Y02W 30/40* (2015.05)

(58) Field of Classification Search
CPC .. C02F 11/04; C02F 2103/20; C02F 2303/10; C07C 9/04; Y02E 50/30; Y02W 30/40

USPC .... 210/603, 612, 613, 620, 252, 259; 71/10, 71/11, 21
See application file for complete search history.

(56) References Cited

FOREIGN PATENT DOCUMENTS

| | | | | |
|---|---|---|---|---|
| KR | 10-1113253 | B1 | 2/2012 | |
| KR | 101342982 | B1 * | 12/2013 | ............ C02F 11/127 |
| KR | 20140004989 | A * | 1/2014 | ............ C02F 3/2893 |
| KR | 20200096830 | A * | 8/2020 | ............... C02F 9/20 |
| KR | 20210041647 | A * | 4/2021 | ............. C05F 17/90 |

(Continued)

OTHER PUBLICATIONS

Machine-generated English translation of KR 20220073015, generated on Aug. 7, 2025.*

(Continued)

*Primary Examiner* — Fred Prince
(74) *Attorney, Agent, or Firm* — NKL Law; Jae Youn Kim

(57) ABSTRACT

The present invention relates to a biogas production system using organic waste, including: a pretreatment facility having a mixed equalization tank adapted to equally mix food waste and livestock manure and treat and produce the mixed food waste and livestock manure as the organic waste; an anaerobic digestion facility having anaerobic digesters adapted to perform anaerobic digestion of the organic waste introduced thereinto; a gas refinery and power plant having a cogeneration plant adapted to perform cogeneration using the biogas produced in the anaerobic digestion facility; a composting and liquefaction facility having a solid-liquid separator adapted to separate the organic waste fed from the anaerobic digesters of the anaerobic digestion facility into liquid and sludge; and an odor treatment facility for purifying the odor emitted from the mixed equalization tank.

5 Claims, 5 Drawing Sheets

(56)     References Cited

FOREIGN PATENT DOCUMENTS

KR       20220073015  A   *   6/2022   ............. B01D 53/84
KR       20230126768  A   *   8/2023   .............. B09B 3/00

OTHER PUBLICATIONS

Machine-generated English translation of KR 20210041647, gen-
erated on Aug. 7, 2025.*
Machine-generated English translation of KR 20230126768, gen-
erated on Aug. 7, 2025.*
Machine-generated English translation of KR 101113253, generated
on Aug. 7, 2025.*
Machine-generated English translation of KR 2020-0096830, gen-
erated on Aug. 7, 2025.*
Machine-generated English translation of KR 2014-0004989, gen-
erated on Aug. 7, 2025.*
Machine-generated English translation of KR 101342982, gener-
ated on Aug. 7, 2025.*

* cited by examiner

BIOGAS PRODUCTION SYSTEM USING ORGANIC WASTE

BACKGROUND OF THE INVENTION

Field of the Invention

The present invention relates to a biogas production system using organic waste, and more specifically, to a biogas production system using organic waste that is capable of handling changes in the amount of organic waste such as food waste and livestock manure fed thereto and having a heat exchanger adapting to keep constant temperature of the organic waste fed to a first anaerobic digester and a second anaerobic digester at 35° C., thereby producing uniform and stabbe biogas even in winter season.

Background of the Related Art

Organic waste such as livestock manure, food waste, and the like may seriously damage environments due to its decomposition and leachate, and accordingly, the organic waste has to be collected necessarily by type and thrown away through a prescribed waste disposal process.

However, simple disposal of the organic waste requires treatment facilities and labors, which undesirably causes larger economic waste rather than productive advantages.

Recently, methods and technologies for recycling organic waste have been developed, and representatively, there are technologies for recycling organic waste to produce compost and for producing biogas using organic waste and turning it into energy.

One of the conventional methods and technologies is disclosed in Korean Patent No. 10-1113253 entitled 'Biogas production system using organic waste, and the conventional biogas production system includes: a feeder for feeding organic waste; a gas producer for fermenting the organic waste fed from the feeder to produce biogas; a liquid fertilizer storage tank for receiving some of the organic waste from the feeder and the gas producer to store the received organic waste as organic waste for a liquid fertilizer and supplementation; and a polluted water handler for purifying the polluted water generated from the organic waste of the feeder, the gas producer, and the liquid fertilizer storage tank.

The gas producer includes: a storage tank for storing the organic waste fed from the feeder and moving the polluted water formed as the upper water of the organic waste stored therein to the polluted water handler; an anaerobic fermentation tank having a first fermentation tank adapted to receive the organic waste from the storage tank, primarily ferment the organic waste, and produce the biogas and a second fermentation tank adapted to receive the organic waste primarily fermented in the first fermentation tank, secondarily ferment the organic waste, and produce the biogas; a gas collection tank for collecting the biogas produced in the anaerobic fermentation tank; and a surplus gas burner for burning, if surplus gas is generated from the anaerobic fermentation tank, the surplus gas.

In this case, the first fermentation tank and the second fermentation tank include: agitators for agitating the organic waste; fermentation circulation lines for re-circulating the organic waste stored therein first to the first fermentation tank; heaters for forming fermentation temperatures of the organic waste circulated therein; and gas conveying ducts for guiding the produced biogas to the gas collection tank.

According to the conventional biogas production system as mentioned above, the organic waste fed thereto is crushed, sorted, and separated into solid and liquid and then fed to the storage tank, and next, the storage tank feeds the organic waste to the anaerobic fermentation tank.

Accordingly, even if the anaerobic fermentation tank is kept to a given temperature using a heat transfer fluid supplied from a cogeneration plant, it becomes decreased at temperature in the process of introducing the cold organic waste of the storage tank therein, thereby undesirably lowering an amount of methane gas produced or producing the methane gas after a certain period of time has passed.

To be specific, the production of the methane gas is gently carried out after the organic waste stays in the anaerobic fermentation tank for 15 to 30 days, but if the cold organic waste of the storage tank is introduced, the organic waste of the anaerobic fermentation tank may be drastically lowered to a temperature below 35° C., thereby reducing an amount of methane gas produced and failing to produce good-quality methane gas.

SUMMARY OF THE INVENTION

Accordingly, the present invention has been made in view of the above-mentioned problems occurring in the related art, and it is an object of the present invention to provide a biogas production system using organic waste that is configured to have heaters disposed inside anaerobic digesters and thus connected to a hot water boiler or a heat exchanger of a cogeneration plant so that the organic waste in the anaerobic digesters is kept constantly to a given temperature to cause microorganisms to grow actively, without any stop, thereby consistently producing good-quality methane gas (hereinafter, referred to as biogas).

It is another object of the present invention to provide a biogas production system using organic waste that is configured to have a heat exchanger connected to a mixed equalization tank and a digestion stabilization tank to allow the organic waste such as livestock manure and food waste to be heated to a given temperature after equally mixed in the mixed equalization tank, so that the temperature of the organic waste feeding to anaerobic digesters is not different from that of the organic waste stored in the anaerobic digesters to cause the microorganisms in the anaerobic digesters to grow actively, thereby uniformly producing stabilized biogas even in winter season.

To accomplish the above-mentioned objects, according to the present invention, there is provided a biogas production system using organic waste, including: a pretreatment facility having a mixed equalization tank adapted to equally mix food waste sorted, crushed and agitated and livestock manure treated in an impurity handler and to treat and produce the mixed food waste and livestock manure as the organic waste; an anaerobic digestion facility having anaerobic digesters adapted to perform anaerobic digestion of the organic waste introduced thereinto from the pretreatment facility; a gas refinery and power plant having a cogeneration plant adapted to perform cogeneration using the biogas produced in the anaerobic digestion facility to thus produce electricity; a composting and liquefaction facility having a solid-liquid separator adapted to separate the organic waste fed from the anaerobic digesters of the anaerobic digestion facility into liquid and sludge to thus produce a liquid fertilizer and compost; and an odor treatment facility having a cleaning device for purifying the odor emitted from the mixed equalization tank.

According to the present invention, desirably, the pretreatment facility may include: a food storage hopper for feeding the food waste introduced thereinto to a shredding sorter; the shredding sorter for primarily shredding and sorting the food waste fed from the food storage hopper; a crusher for secondarily crushing the food waste sorted by the shredding sorter; a pulping and agitation tank for agitating the food waste crushed by the crusher; the impurity handler for sorting impurities from the livestock manure introduced thereinto; and the mixed equalization tank for equally mixing the food waste fed from the pulping and agitation tank and the livestock manure fed from the impurity handler.

According to the present invention, desirably, the anaerobic digestion facility may include: the first and second anaerobic digesters adapted to perform the anaerobic digestion of the organic waste fed from the mixed equalization tank of the pretreatment facility to thus produce the biogas; heaters connected to a heat exchanger of the cogeneration plant and a hot water boiler of the gas refinery and power plant to allow the organic waste in the first anaerobic digester and the second anaerobic digester to be kept to a given temperature; a heat exchanger connected to the mixed equalization tank of the pretreatment facility and a digestion stabilization tank of the composting and liquefaction facility to heat the organic waste of the mixed equalization tank using the heat generated from the digestion stabilization tank; and agitators disposed inside the first anaerobic digester and the second anaerobic digester to periodically agitate the organic waste.

According to the present invention, desirably, the first anaerobic digester and the second anaerobic digester may have gas safety valves installed on one side thereof to automatically exhaust the biogas when an excessive pressure occurs and solids feeders installed on the other side thereof to additionally feed organic solid waste if necessary.

According to the present invention, desirably, the gas refinery and power plant may include: a gas storage tank for collecting and storing the biogas produced in the first anaerobic digester and the second anaerobic digester; a desulfurization facility for desulfurizing the biogas fed from the gas storage tank; a dehumidification facility for separating humidity from the biogas desulfurized in the desulfurization facility; and the cogeneration plant for performing the cogeneration using the biogas dehumidified in the dehumidification facility.

According to the present invention, desirably, the composting and liquefaction facility may include: the digestion stabilization tank for storing and stabilizing the organic waste discharged after the use in the first anaerobic digester and the second anaerobic digester; the solid-liquid separator for separating the organic waste stabilized by the digestion stabilization tank into the sludge and liquid; a mixer for mixing the sludge separated by the solid-liquid separator; a compost fermentation tank for fermenting the sludge mixed by the mixer so as to produce compost; a high-speed fermenter for fermenting the liquid separated by the solid-liquid separator after a flow of liquid transferred has been adjusted through a flow control tank; an aerobic reactor for aging the liquid fermented by the high-speed fermenter to make a liquid fertilizer; and a liquid manure storage tank for storing the liquid fertilizer produced by the aerobic reactor.

BRIEF DESCRIPTION OF THE DRAWINGS

The above and other objects, features and advantages of the present invention will be apparent from the following detailed description of the preferred embodiments of the invention in conjunction with the accompanying drawings, in which.

DETAILED DESCRIPTION OF THE PREFERRED EMBODIMENTS

Now, the present invention will be explained in detail with reference to the attached drawings.

The present invention relates to a biogas production system that equally mixes food waste generated in houses and restaurants and livestock manure generated in livestock farms, pig farms, poultry farms, and the like in a mixed equalization tank to obtain organic waste and then produces biogas with the organic waste in a plurality of anaerobic digesters, so that the biogas is used as a heat transfer fluid of a cogeneration plant, thereby producing electricity.

Further, the present invention relates to the biogas production system that separates the organic waste thrown away after the biogas has been produced therefrom in the anaerobic digesters into sludge and liquid to thus produce compost and a liquid fertilizer.

Figure 1:
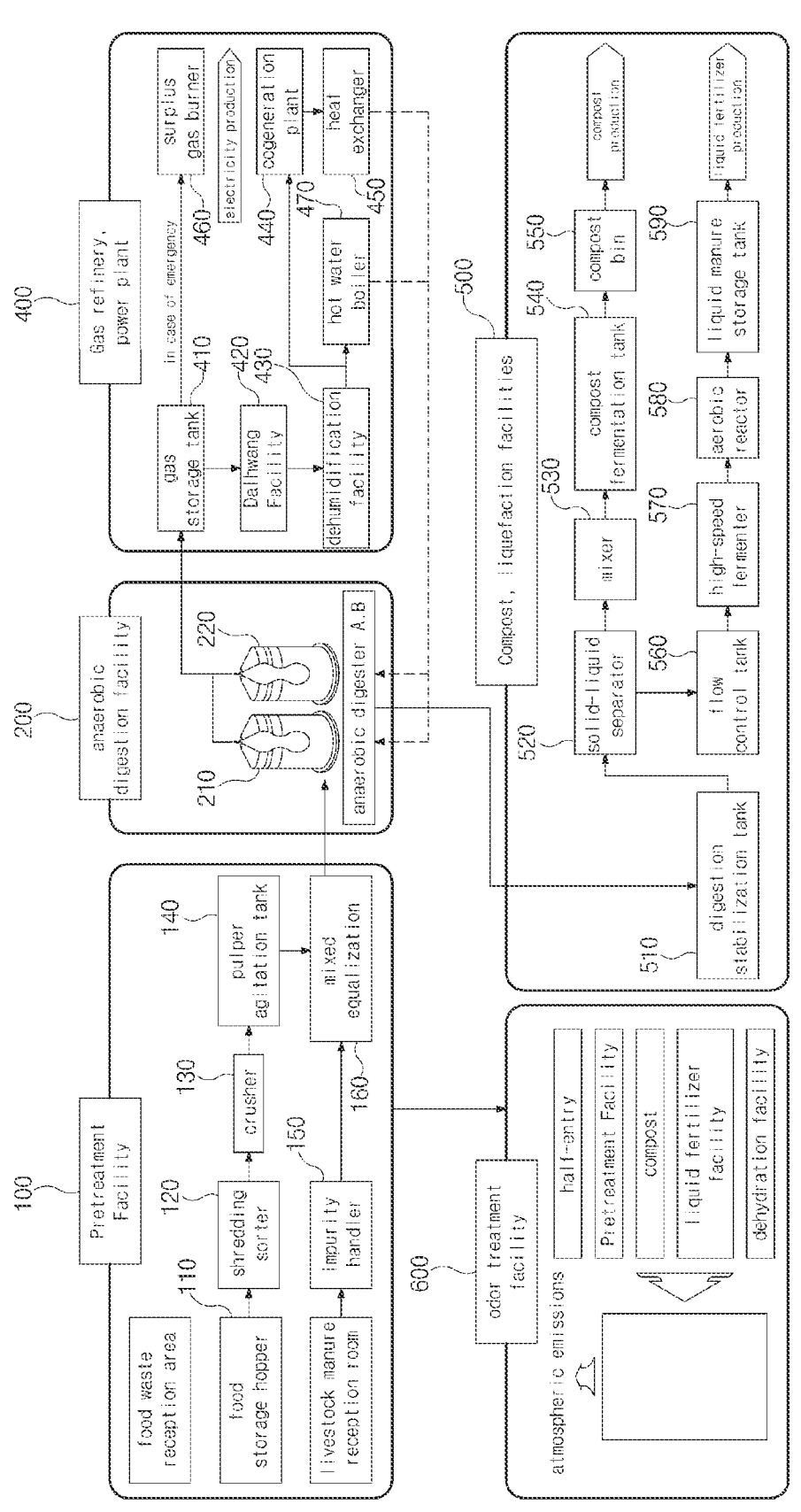
FIG. 1 is a block diagram showing a biogas production system using organic waste according to the present invention.
Figure 2:
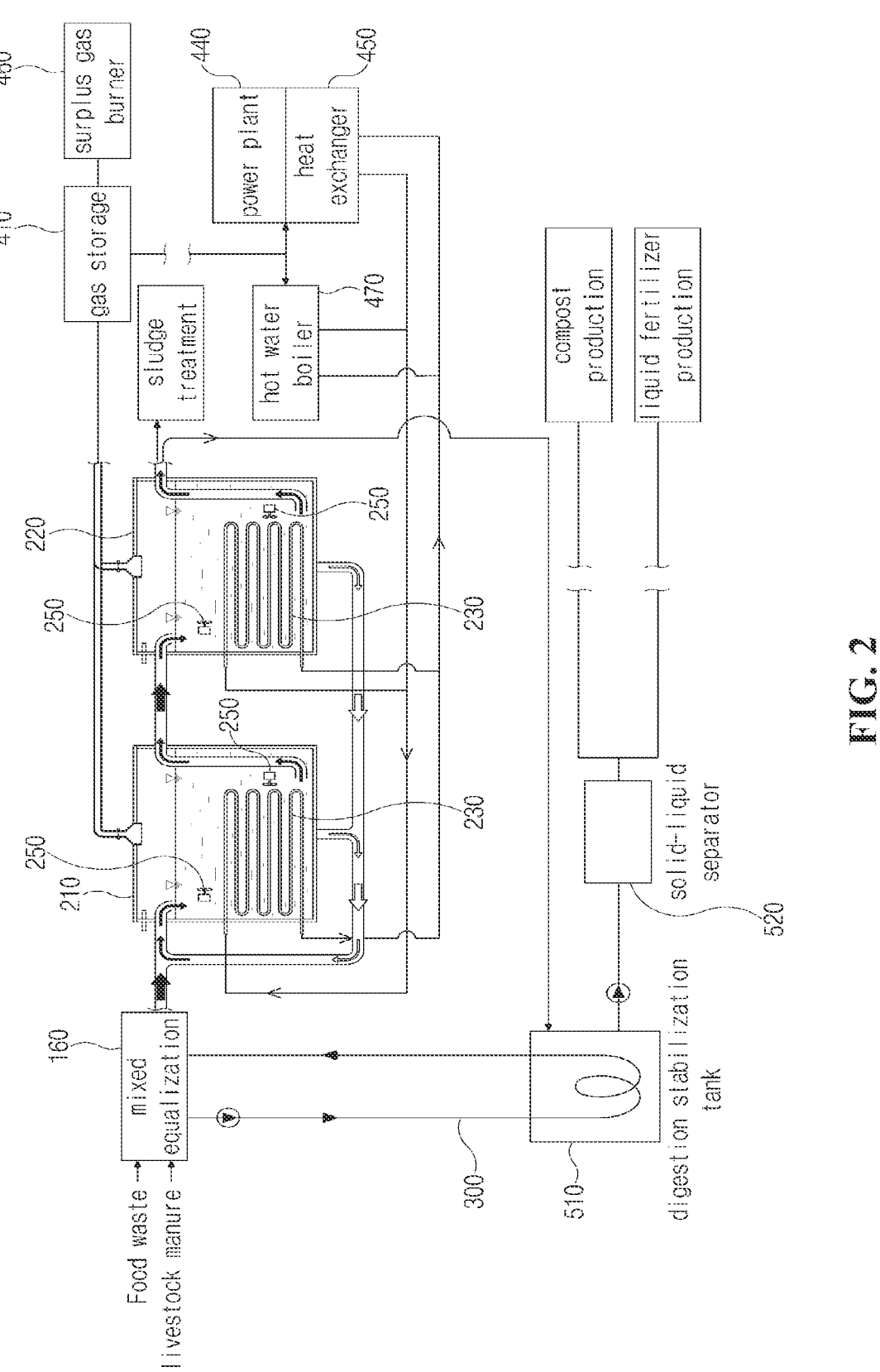
FIG. 2 is a schematic block diagram showing a circulation structure of anaerobic digesters and heaters of the biogas production system using organic waste according to the present invention.

FIG. 1 is a block diagram showing a biogas production system using organic waste according to the present invention, and FIG. 2 is a schematic block diagram showing a circulation structure of anaerobic digesters and heaters of the biogas production system using organic waste according to the present invention.

Referring to FIGS. 1 and 2, a biogas production system using organic waste according to the present invention largely includes: a pretreatment facility 100, an anaerobic digestion facility 200, a gas refinery and power plant 400, a composting and liquefaction facility 500, and an odor treatment facility 600.

First, the entire treatment process of the biogas production system according to the present invention will be described with reference to FIG. 1.

Food waste as organic waste is fed to a food storage hopper 110 of the pretreatment facility 100 through feeding means such as a conveyor, a conveying screw, or the like, and the feeding means is a feeding device generally used in industrial fields. Accordingly, an explanation and illustration of the feeding means will be avoided.

The food waste fed to the food storage hopper 110 moves to a shredding sorter 120, a crusher 130, and a pulping and agitation tank 140 sequentially, so that the food waste is subjected to primary shredding and sorting through the shredding sorter 120, to secondary shredding through the crusher 130, and to agitation through the pulping and agitation tank 140. Further, the pretreatment facility 100 includes an impurity handler 150 for handling impurities mixed in livestock manure of the organic waste introduced through a separate line and a mixed equalization tank 160 for equally mixing the agitated food waste and the livestock manure handled in the impurity handler 150.

The pretreatment facility 100 is configured to allow the shredding sorter 120, the crusher 130, and the pulping and agitation tank 140, and the impurity handler 150 to be installed as pretreatment devices in a single room.

The pulping and agitation tank 140 is a gravity separator for sorting soil, sand, iron powder, shells, and the like contained in the food waste through gravity differences.

The reason why the pretreatment facility 100 is installed in the single room is that air in the room from which odor is generated is purified through the odor treatment facility 600 installed on one side of the pretreatment facility 100.

The anaerobic digestion facility 200 includes a first anaerobic digester 210 and a second anaerobic digester 220 adapted to allow the organic waste treated in the pretreatment facility 100 and fed therefrom to be subjected to anaerobic digestion to thus produce biogas.

In this case, two or more anaerobic digesters may be installed in the anaerobic digestion facility 200 according to installation environments and amounts of organic waste fed and treated.

The gas refinery and power plant 400 is configured to have a cogeneration plant 440 adapted to perform cogeneration using the biogas produced in the anaerobic digestion facility 200 to thus produce electricity.

Next, the composting and liquefaction facility 500 has a solid-liquid separator 520 adapted to separate the organic waste sludge generated in the first anaerobic digester 210 and the second anaerobic digester 220 of the anaerobic digestion facility 200 into liquid and sludge to thus produce a liquid fertilizer and compost.

The odor treatment facility 600, which serves to purify the odor generated in the pretreatment facility 100, has a cleaning tank (not shown) in which the odor remaining in the room of the pretreatment facility 100 is introduced into the lower portion thereof, passes through water sprayed from nozzles and a filtering device, while moving to the upper portion thereof, and thus exhausted to the outside, thereby emitting the odor to the outside of the pretreatment facility 100.

The respective facilities of the biogas production system using organic waste according to the present invention will be described in detail below.

The pretreatment facility 100 sorts the food waste and the livestock manure as the organic waste and crushes and mixes them.

The pretreatment facility 100 has treatment lines divided into a first line for treating the food waste and a second line for treating the livestock manure.

Accordingly, on the first line are installed the food storage hopper 110 for feeding the food waste introduced thereinto to the shredding sorter 120, the shredding sorter 120 for primarily shredding the food waste fed from the food storage hopper 110, the crusher 130 for secondarily crushing the food waste sorted from the shredding sorter 120, and the pulping and agitation tank 140 for mixing the food waste secondarily crushed in the crusher 130.

The pulping and agitation tank 140 serves as the gravity sorter adapted to sort inorganic compounds contained in the food waste introduced thereinto.

Further, on the second line is installed the impurity handler 150 adapted to sort the impurities contained in the livestock manure and thus treat the livestock manure.

The food waste treated on the first line and the livestock manure treated on the second line move to the mixed equalization tank 160 so that they are equally mixed and treated.

The food waste and livestock manure equally treated in the pretreatment facility 160 is now called organic waste.

Further, the anaerobic digestion facility 200 is a place in which microorganisms grow in the organic waste fed from the pretreatment facility 100 through the first anaerobic digester and the second anaerobic digester to thus produce biogas.

The anaerobic digestion facility 200 includes the first anaerobic digester 210 and the second anaerobic digester 220 for performing the anaerobic digestion of the organic waste fed from the mixed equalization tank 160 of the pretreatment facility 100, heaters 230 connected to a heat exchanger 450 of the cogeneration plant 440 and a hot water boiler 470 to allow a temperature of the organic waste to be kept to 35° C., and agitators 250 disposed inside the first anaerobic digester 210 and the second anaerobic digester 220 to periodically agitate the organic waste.

The heaters 230 disposed in the first anaerobic digester 210 and the second anaerobic digester 220 are connected to the heat exchanger 450 of the cogeneration plant 440 and the hot water boiler 470 and selectively open if necessary.

The biogas produced in the first anaerobic digester 210 and the second anaerobic digester 220 is supplied to the cogeneration plant 440 and the hot water boiler 470, so that the cogeneration plant 440 and the hot water boiler 470 operate.

The cogeneration plant 440 receives the biogas to produce electricity, re-circulates the waste heat generated in a process of burning the biogas to the heat exchanger 450 to heat the water of the heat exchanger 450, circulates the heated water through the connection to the heaters 230 disposed inside the first anaerobic digester 210 and the second anaerobic digester 220, so that the organic waste in the first anaerobic digester 210 and the second anaerobic digester 220 has an optimal temperature at which the microorganisms grow.

In this case, the heaters 230 disposed inside the first anaerobic digester 210 and the second anaerobic digester 220 are located in parallel with the heat exchanger 450 of the cogeneration plant 440 and the hot water boiler 470 located on one side thereof, so that if necessary, they are selectively connected to the heat exchanger 450 and the hot water boiler 470.

To be specific, if the heat exchanger 450 of the cogeneration plant 440 does not work, the hot water boiler 470 operates to supply hot water to the heaters 230 so that the organic waste in the first anaerobic digester 210 and the second anaerobic digester 220 is kept constantly to the temperature of 35° C.

Electrical and electronic systems for allowing the heaters 230 disposed inside the first anaerobic digester 210 and the second anaerobic digester 220 to be kept constantly to the temperature of 35° C. may be adopted in the technologies well known in the industrial fields, and therefore, an explanation of the electrical and electronic systems will be avoided.

The gas refinery and power plant 400 operates the cogeneration plant 440 using the biogas produced in the first anaerobic digester 210 and the second anaerobic digester 220 and thus produces electricity.

To be specific, the gas refinery and power plant 400 includes a gas storage tank 410 for collecting and storing the biogas produced in the first anaerobic digester 210 and the second anaerobic digester 220, a desulfurization facility 420 for desulfurizing the biogas fed from the gas storage tank 410, a dehumidification facility 430 for separating humidity from the biogas desulfurized in the desulfurization facility 420, and the cogeneration plant 440 for performing cogeneration using the biogas dehumidified in the dehumidification facility 430.

The gas storage tank 410 collects and stores the biogas produced in the first anaerobic digester 210 and the second anaerobic digester 220, and if all biogas is not stored in the gas storage tank 410 due to excessive production thereof, the surplus biogas is burnt in a surplus gas burner 460 installed on one side of the gas storage tank 410 and thus exhausted to the air.

Figure 3:
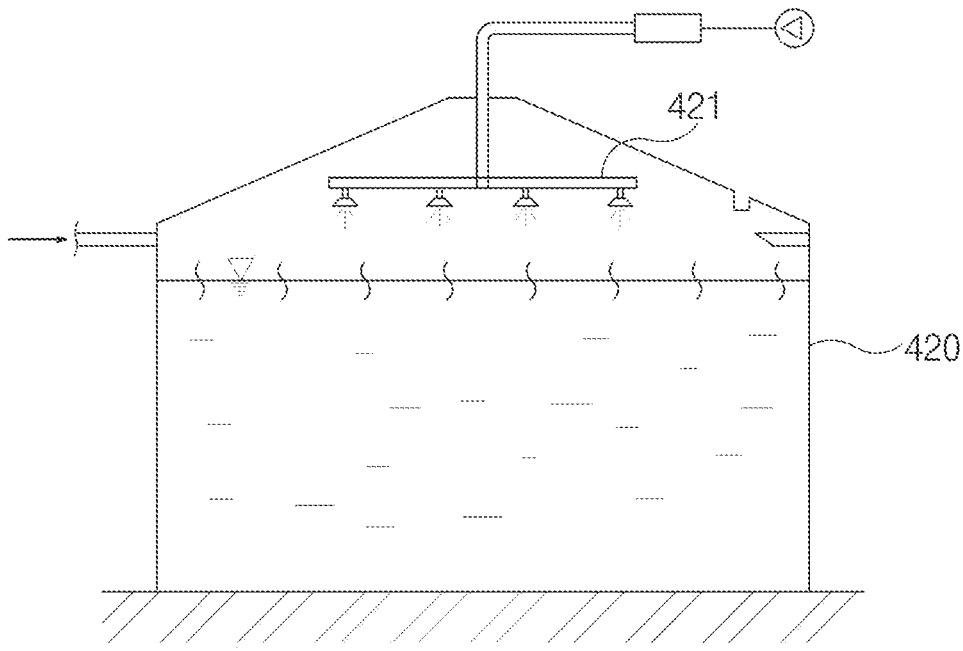
FIG. 3 is a sectional view showing a desulfurization facility for the biogas produced in the anaerobic digesters according to the present invention.
Figure 4:
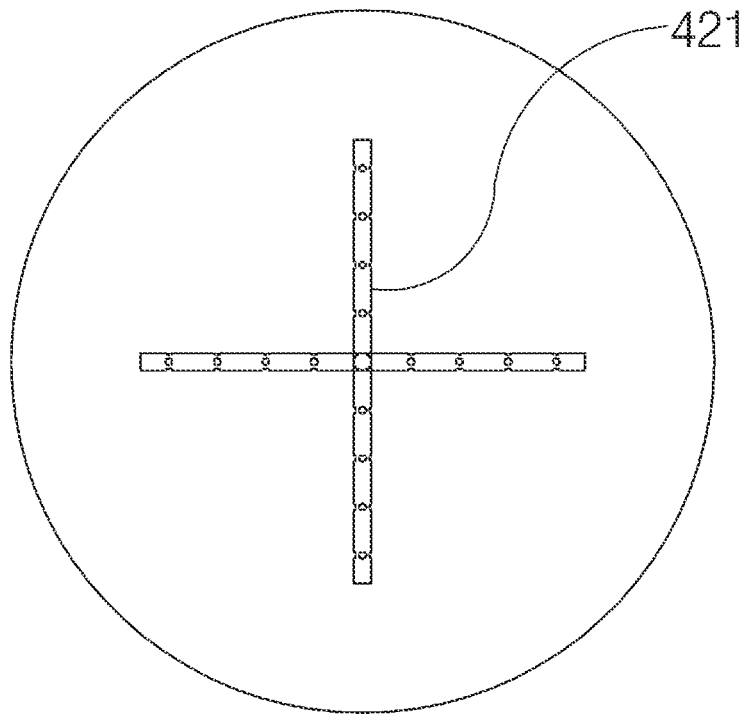
FIG. 4 is a bottom view showing air injection nozzles of the desulfurization facility according to the present invention.

FIG. 3 is a sectional view showing a desulfurization facility for the biogas produced in the anaerobic digesters according to the present invention and FIG. 4 is a bottom view showing air injection nozzles of the desulfurization facility according to the present invention. As shown, the desulfurization facility 420 is configured to separate hydrogen sulfide mixed in the biogas fed to the cogeneration plant 440 from the gas storage tank 410 so that only pure biogas can be fed.

The desulfurization facility 420 stores water therein and has a plurality of air injection nozzles 421 located above the water to inject air into the biogas introduced thereinto, so that the hydrogen sulfide is separated from the biogas and enters the water, thereby transferring only pure biogas to the cogeneration plant 440.

The air injection nozzles 421 of the desulfurization facility 420 may be replaced with fog injection nozzles, so that fog sprays onto the biogas to separate the hydrogen sulfide mixed in the biogas.

The biogas desulfurized in the desulfurization facility 420 is separated from moisture in the dehumidification facility 430 so that only pure biogas is fed to the cogeneration plant 440.

Further, the composting and liquefaction facility 500 as shown in FIG. 1 serves to produce, as a liquid fertilizer and compost, the organic waste remaining after the biogas has been produced from the organic waste in the first anaerobic digester 210 and the second anaerobic digester 220, and accordingly, the composting and liquefaction facility 500 has a liquid fertilizer production line for producing a liquid fertilizer and a compost production line for producing compost.

The composting and liquefaction facility 500 includes a digestion stabilization tank 510 for storing and stabilizing the organic waste discharged after the use in the first anaerobic digester 210 and the second anaerobic digester 220 and a solid-liquid separator 520 for separating the organic waste stabilized by the digestion stabilization tank 510 into sludge and liquid.

The organic waste in the solid-liquid separator 520 is treated dividedly into the compost production line and the liquid fertilizer production line.

On the compost production line divided by the solid-liquid separator 520 are installed a mixer 530 for mixing the sludge and a compost fermentation tank 540 for fermenting the sludge mixed by the mixer 530 so as to produce the compost.

On the liquid fertilizer production line are installed a flow control tank 560 for adjusting a flow of liquid separated by the solid-liquid separator 520, a high-speed fermenter 570 for fermenting the liquid whose flow is adjusted, an aerobic reactor 580 for aging the liquid fermented by the high-speed fermenter 570 to make the liquid fertilizer, and a liquid manure storage tank 590 for storing the liquid fertilizer produced by the aerobic reactor 580.

Further, a heat exchanger 300 is connected to the digestion stabilization tank 510 and the mixed equalization tank 160, and in winter season or in cold weather, accordingly, the heat in the digestion stabilization tank 510 moves to the mixed equalization tank 160 and thus heats the organic waste of the mixed equalization tank 160, so that when the organic waste of the mixed equalization tank 160 is introduced into the first anaerobic digester 210, the temperature of the organic waste in the first anaerobic digester 210 does not fall, thereby consistently and equally producing the biogas, while the digestion through the microorganisms is being carried out, without any stop.

To be specific, pipes of the heat exchanger 300 are connected to the digestion stabilization tank 510 and the mixed equalization tank 160, and accordingly, the organic waste of the mixed equalization tank 160 moves along the pipes and has heat exchanging in the digestion stabilization tank 510. Next, the organic waste moves to the mixed equalization tank 160, and accordingly, the organic waste in the mixed equalization tank 160 is kept to the temperature of 35° C.

The organic waste of the first anaerobic digester 210 and the second anaerobic digester 220 are kept to the temperature of 35° C. so as to allow aerobic digestion through the microorganisms to be actively generated. If the organic waste in the mixed equalization tank 160 is fed to a temperature lower than 35° C., the activities of the microorganisms in the organic waste of the first anaerobic digester 210 are stopped to thus reduce an amount of biogas produced.

According to the present invention, the temperature of the organic waste of the first anaerobic digester 210 is kept equally to the temperature of the organic waste of the mixed equalization tank 160, so that the digestion of the microorganisms in the first anaerobic digester 210 and the second anaerobic digester 220 is consistently performed, without any stop, thereby regularly producing the amount of biogas, irrespective of a temperature difference by season.

Figure 5:
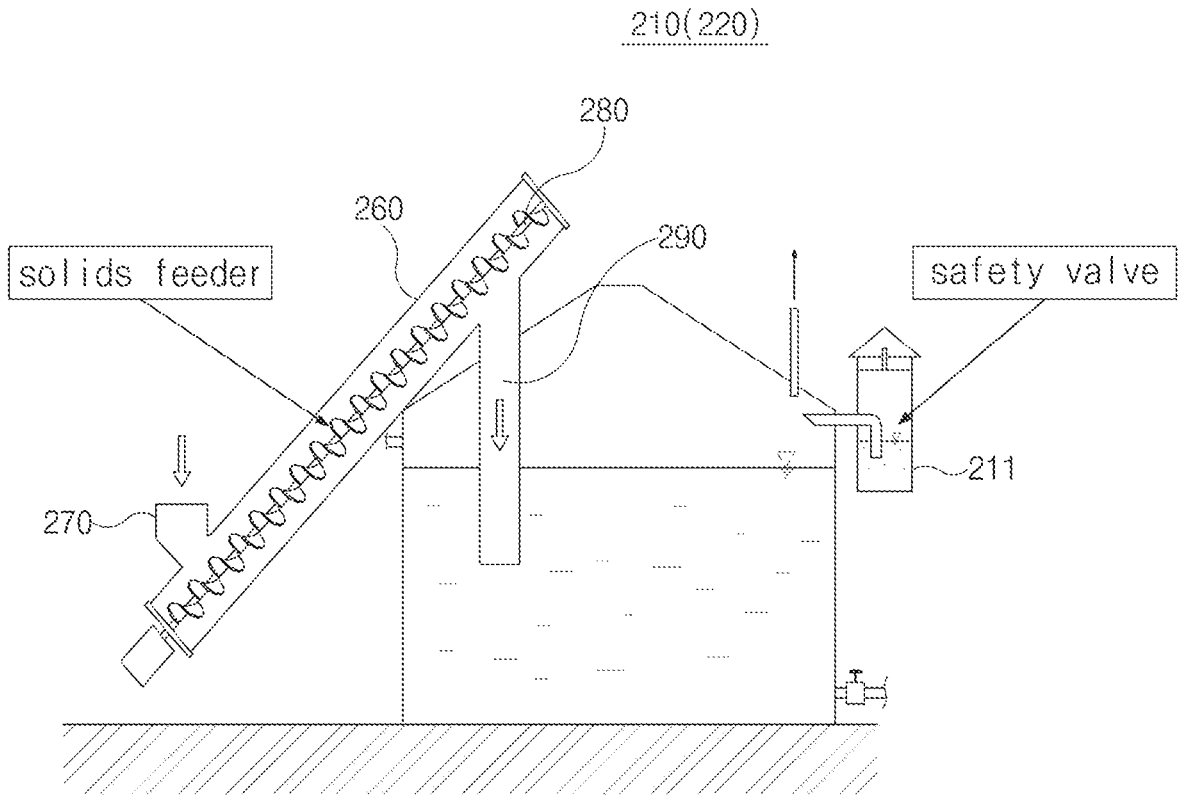
FIG. 5 is an exemplary view showing a solids feeder installed on one side of the anaerobic digesters according to the present invention.

FIG. 5 is an exemplary view showing a solids feeder installed on one side of the anaerobic digesters according to the present invention. To be specific, a gas safety valve 211 is installed on one side of the first anaerobic digester 210 and the second anaerobic digester 220 to automatically exhaust the biogas when an excessive pressure occurs, and the solids feeder 260 is installed on the other side thereof to additionally feed organic solid waste if necessary.

If the biogas produced in the first anaerobic digester 210 and the second anaerobic digester 220 is excessively larger than the amount of gas introduced into the gas storage tank 410 to thus cause expansion, the gas safety valve 211, which is installed on one side of the first anaerobic digester 210 and the second anaerobic digester 220, serves to automatically exhaust the biogas, so that a safety accident such as a gas explosion accident caused by the expansion can be prevented.

Further, the solids feeder 260, which is installed on the other side of the first anaerobic digester 210 and the second anaerobic digester 220, serves to additionally feed organic solid waste.

The solids feeder 260 is used as an emergency feeder when the organic waste to the first anaerobic digester 210 and the second anaerobic digester 220 is supplemented because of a lack of the organic waste or the feeding of the organic waste is stopped due to the failure of the pretreatment facility 100.

The solids feeder 260 includes a pipe-shaped conveying screw 280, a feeding hopper 270 disposed on the lower portion of the conveying screw 280, and a feeding pipe 290 protruding vertically and downwardly from the upper portion of the conveying screw 280, and accordingly, the solids feeder 260 feeds the organic solid waste in case of emergency.

According to the present invention, the anaerobic digestion facility 200 is configured to have the first anaerobic digester 210 for receiving the organic waste from the mixed equalization tank 160 to primarily ferment the organic waste and the second anaerobic digester 220 for receiving the organic waste primarily fermented in the first anaerobic digester 210 to secondarily ferment the organic waste.

The first anaerobic digester 210 and the second anaerobic digester 220 as described in the present invention are just exemplary, and two or more anaerobic digesters may be provided according to the amounts of organic waste treated.

According to the present invention, the agitators 250 are disposed inside the first anaerobic digester 210 and the second anaerobic digester 220 to periodically agitate the organic waste, and they move up and down to equally mix the organic waste so that the organic waste can be uniformly fermented.

According to the present invention, the biogas production system using the organic waste can produce stabilized biogas, while freely handling changes in the amount of organic waste fed thereto.

According to the present invention, further, the heat exchanger is connected to the mixed equalization tank and the digestion stabilization tank to allow the organic waste fed to the first anaerobic digester and the second anaerobic digester to be kept to the temperature of 35° C., thereby uniformly producing stabilized biogas even in winter season.

As described above, the biogas production system is configured to allow the food waste and the livestock manure to be treated in the anaerobic digesters to produce biogas and to move the biogas to the cogeneration plant to produce electricity, while separating the organic waste after the use in the anaerobic digesters into the sludge and liquid so that the sludge is converted into compost and the liquid into a liquid fertilizer, thereby preventing occurrence of environmental pollution and providing eco-friendly clean energy.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention. It should be understood that the invention covers all the modifications, equivalents, and replacements within the idea and technical scope of the invention.

What is claimed is:

1. A biogas production system using organic waste, comprising:

a pretreatment facility having a mixed equalization tank adapted to equally mix food waste sorted, crushed and agitated and livestock manure treated in an impurity handler and to treat and produce the mixed food waste and livestock manure as the organic waste;

an anaerobic digestion facility having anaerobic digesters adapted to perform anaerobic digestion of the organic waste introduced thereinto from the pretreatment facility;

a gas refinery and power plant having a cogeneration plant adapted to perform cogeneration using the biogas produced in the anaerobic digestion facility to thus produce electricity;

a composting and liquefaction facility having a solid-liquid separator adapted to separate the organic waste fed from the anaerobic digesters of the anaerobic digestion facility into liquid and sludge to thus produce a liquid fertilizer and compost; and an odor treatment facility having a cleaning device for purifying the odor emitted from the mixed equalization tank, wherein the pretreatment facility comprises:

a food storage hopper for feeding the food waste introduced thereinto to a shredding sorter;

the shredding sorter for primarily shredding and sorting the food waste fed from the food storage hopper;

a crusher for secondarily crushing the food waste sorted by the shredding sorter;

a pulping and agitation tank for agitating the food waste crushed by the crusher;

the impurity handler for sorting impurities from the livestock manure introduced thereinto; and the mixed equalization tank for equally mixing the food waste fed from the pulping and agitation tank and the livestock manure fed from the impurity handler.

2. A biogas production system using organic waste, comprising:

a pretreatment facility having a mixed equalization tank adapted to equally mix food waste sorted, crushed and agitated and livestock manure treated in an impurity handler and to treat and produce the mixed food waste and livestock manure as the organic waste;

an anaerobic digestion facility having anaerobic digesters adapted to perform anaerobic digestion of the organic waste introduced thereinto from the pretreatment facility;

a gas refinery and power plant having a cogeneration plant adapted to perform cogeneration using the biogas produced in the anaerobic digestion facility to thus produce electricity;

a composting and liquefaction facility having a solid-liquid separator adapted to separate the organic waste fed from the anaerobic digesters of the anaerobic digestion facility into liquid and sludge to thus produce a liquid fertilizer and compost; and an odor treatment facility having a cleaning device for purifying the odor emitted from the mixed equalization tank, wherein the anaerobic digestion facility comprises:

a first anaerobic digester and a second anaerobic digester adapted to perform the anaerobic digestion of the organic waste fed from the mixed equalization tank of the pretreatment facility to thus produce the biogas;

heaters connected to a heat exchanger of the cogeneration plant and a hot water boiler of the gas refinery and power plant to allow the organic waste in the first anaerobic digester and the second anaerobic digester to be kept to a given temperature;

a heat exchanger connected to the mixed equalization tank of the pretreatment facility and a digestion stabilization tank of the composting and liquefaction facility to heat the organic waste of the mixed equalization tank using the heat generated from the digestion stabilization tank; and agitators disposed inside the first anaerobic digester and the second anaerobic digester to periodically agitate the organic waste.

3. The biogas production system according to claim 2, wherein the first anaerobic digester and the second anaerobic digester have gas safety valves installed on one side thereof to automatically exhaust the biogas when an excessive pressure occurs and solids feeders installed on the other side thereof to additionally feed organic solid waste.

4. The biogas production system according to claim 2, wherein the gas refinery and power plant comprises:

a gas storage tank for collecting and storing the biogas produced in the first anaerobic digester and the second anaerobic digester;

a desulfurization facility for desulfurizing the biogas fed from the gas storage tank;

a dehumidification facility for separating humidity from the biogas desulfurized in the desulfurization facility; and the cogeneration plant for performing the cogeneration using the biogas dehumidified in the dehumidification facility.

5. The biogas production system according to claim 2, wherein the composting and liquefaction facility comprises:

the digestion stabilization tank for storing and stabilizing the organic waste discharged after the use in the first anaerobic digester and the second anaerobic digester;

the solid-liquid separator for separating the organic waste stabilized by the digestion stabilization tank into the sludge and liquid;

a mixer for mixing the sludge separated by the solid-liquid separator;

a compost fermentation tank for fermenting the sludge mixed by the mixer so as to produce compost;

a high-speed fermenter for fermenting the liquid separated by the solid-liquid separator after a flow of liquid transferred has been adjusted through a flow control tank;

an aerobic reactor for aging the liquid fermented by the high-speed fermenter to make a liquid fertilizer; and a liquid manure storage tank for storing the liquid fertilizer produced by the aerobic reactor.

\* \* \* \* \*